United States Patent
Muto et al.

(12)

(10) Patent No.: US 6,278,106 B1
(45) Date of Patent: Aug. 21, 2001

(54) OPTICAL SENSOR AND SENSING METHOD

(76) Inventors: Shinzo Muto; Masayuki Morisawa, both of 4-3-11 Takeda, Kofu-Shi, Yamanashi; Hideaki Machida, Tri Chemical Laboratory, Inc., 8154-217, Uenhara, Uenohara-machi, Kitatsurugun, Yamanashi 409-01; Chuanxin Liang, Tri Chemical Laboratory, Inc., 8154-217, Uenhara, Uenohara-machi, Kitatsurugun, Yamanashi 409-01; Noda Naoto, Tri Chemical Laboratory, Inc., 8154-217 Uenhara, Uenohara-machi, Kitatsurugun, Yamanashi 409-01, all of (JP)

( * ) Notice: Subject to any disclaimer, the term of this patent is extended or adjusted under 35 U.S.C. 154(b) by 0 days.

(21) Appl. No.: 09/123,207

(22) Filed: Jul. 27, 1998

(30) Foreign Application Priority Data

Jul. 28, 1997 (JP) .................................................. 9-201880

(51) Int. Cl.$^7$ .............................. G01N 21/00; G02B 6/02
(52) U.S. Cl. ........................................ 250/227.14; 385/12
(58) Field of Search .......................... 250/227.11, 227.14, 250/227.16, 227.17, 227.18, 227.19, 227.21, 227.23, 227.24, 227.25, 231.1; 385/12, 13, 123, 124, 126, 127, 128, 141, 142, 143, 144, 145

(56) References Cited

U.S. PATENT DOCUMENTS

| | | | |
|---|---|---|---|
| 4,040,749 | * | 8/1977 | David et al. .......................... 356/437 |
| 4,399,099 | * | 8/1983 | Buckles ................................. 422/58 |
| 4,492,121 | * | 1/1985 | Lehto ..................................... 73/705 |
| 4,542,987 | * | 9/1985 | Hirschfeld ............................. 356/44 |
| 4,846,548 | * | 7/1989 | Klainer ................................. 385/12 |
| 5,026,139 | * | 6/1991 | Klainer et al. ....................... 356/128 |
| 5,253,037 | * | 10/1993 | Klainer et al. ....................... 356/133 |
| 5,268,972 | * | 12/1993 | Tabacco et al. ....................... 385/12 |
| 5,315,672 | * | 5/1994 | Padovani ............................... 385/12 |
| 5,436,167 | * | 7/1995 | Robillard ............................. 436/165 |
| 5,828,798 | * | 10/1998 | Hopenfeld ............................. 385/12 |
| 5,903,685 | * | 5/1999 | Jones et al. ........................... 385/12 |

* cited by examiner

*Primary Examiner*—John R. Lee
(74) *Attorney, Agent, or Firm*—Jay P. Hendrickson (57) ABSTRACT

The optical sensor of the present invention detects both the existence and concentration of substances by changing from light leakage mode to wave guide mode when the sensor is exposed to the substances to be detected. The changes in the mode results in a large change in optical output. This change is measured and the substance is identified and/or measured with high sensitivity.

The change in light leakage mode to wave guide mode of the sensor is possible by having a clad material around the core material, with the clad material decreasing in the index of refraction when exposed to the substance to be detected. When the index of refraction of the clad becomes less than that of the core material, the sensor changes from the light leakage mode and operates in the wave guide mode. Changes in light intensity output from the sensor is measured over time, and correlated to the substance to be detected.

8 Claims, 6 Drawing Sheets

OPTICAL SENSOR AND SENSING METHOD

FIELD OF THE INVENTION

The present invention relates to the field of optical sensors.

BACKGROUND OF THE INVENTION

The use of sensors to detect chemical substances both qualitatively as well as quantitatively is a growing field. Sensor use is not limited to industrial sectors. Sensors are used in air pollution studies, medical hygiene and numerous other fields.

Many of the existing sensors are electrically driven, and thus have safety problems. For example, many of the submersion sensors are electrical devices and thus have the possibility of current leakage when immersed in water. Other electrically driven sensors, such as alarm sensors that use metallic conductors, cannot be used due to the existence of an electromagnetic field.

Optical fibers have been typically used to transmit light. The theory of the optical transmission in optical fibers is complex. Generally, however, as light enters the end of a long optical fiber, some of the light will travel in a straight axial path thorough the center of the fiber, while the remaining light will come in at various reflection angles and does not follow a straight path as it is reflected from the outer surface of the fiber. The speed of light divided by the index of refraction is the speed of light in the medium. Thus, light traveling through a lower index of refraction material will go faster than that traveling thorough a high index of refraction material. Light traveling in a straight line in the optical fiber will go the longest distance. To make sure that all the light in the optical fiber travels the same distance, the index of refraction is varied throughout the thickness of the fiber. When a cross section of the fiber is taken, the index of refraction will be the greatest at the center of the fiber, and smallest at the outer edge of the fiber, so that the light traveling through the center will be the slowest, and the light traveling through the outer edge, coming in at the greatest reflection angle and thus having the most distance to travel, will be the fastest. In an ideal optical fiber, the total optical intensity of the optical input is equal to the total output intensity.

Optical fiber has been used for sensors. An example of a sensor that uses transmission loss properties of optical fibers is a submersion sensor described in a Japanese patent (Oitsukai)Showa62-25845. However, since the submersion sensors that use the optical fibers require a plate in contact with the optical fiber, the submersion sensor area is very large. This submersion sensor lacks flexibility of use. Other problems with these sensors include the high cost and the time required to fabricate the device.

Japanese patent (tokukai)Hei3-502610 describes a sensor to analyze chemical composition using optical fibers. This patent describes a commonly used theory to make sensors. The internal reflective properties of the optical fibers change as the chemical is absorbed into the fiber. The changes in the internal reflective properties results in changes in the emission intensity of the optical fiber, and that change is measured quantitatively and related to the chemical composition.

The optical sensor described in U.S. Pat. Nos. 4,492,121 and 4,542,987 contains a material that fluoresces on the end of the fiber. The fiber transmits both the excited signal and the response signal.

The U.S. Pat. No. 4,040,749 describes an optical fiber sensor with a wave guide path. A liquid crystal material is attached to the surface of the optical fiber that changes the light transmission property of the wave guide.

U.S. Pat. No. 4,399,099 describes a fiber sheath sensor that quantitatively analyzes the different reaction types of the chemicals being detected in a liquid. This device transmits electromagnetic energy, and contains one or more transmitting or semi-transmitting sheath.

The common characteristic of the optical sensors such as those described above is that they measure small changes in the reflection angles and intensity resulting from a change in the overall reflection condition in the fiber.

However, the drawback of these methods is the limit in the measurement sensitivity since these changes in the reflection angles and intensities are very small. Thus, a sensor needs to be developed which has much higher sensitivity and that can be used in wide range of applications.

For hydrocarbon and other neutral solvents, the reactivity with any other chemicals is minimal. Thus, it is difficult to fabricate a sensor which utilizes reactivity with these materials to change the optical properties of the fiber. At present, there are no simple detection methods for such substances other then very specialized methods.

In addition, there are no sensors that can constantly monitor deadly poisonous gases such as arsine and phosphine except for the use of experimental test papers. The performance of semiconductor devices is related to the concentration of gases used during the semiconductor manufacturing. However, since there is no method to measure such concentration, it is difficult to conduct research to understand the mechanism of the relationship between the concentration of gases and the device characteristics of the semiconductors. Consequently, the development of a new sensor is needed that can be applied to areas where sensors have not previously been used.

The sensor of the present invention overcomes the limitations of prior sensors by providing improved measurement sensitivity, and a wide range of optical applications including the capability to measure neutral solvents and the ability to monitor poisonous gases which was previously not possible.

SUMMARY OF THE PRESENT INVENTION

The optical sensor of the present invention detects both the existence and concentration of substances by changing from light leakage mode to wave guide mode when the sensor is exposed to the substances to be detected. The changes in the mode results in a large change in optical output. This change is measured and the substance is identified and/or measured with high sensitivity.

The change in light leakage mode to wave guide mode of the sensor is possible by having a clad material around the core material, with the clad material decreasing in the index of refraction when exposed to the substance to be detected. When the index of refraction of the clad becomes less than that of the core material, the sensor changes from the light leakage mode and operates in the wave guide mode. Changes in light intensity output from the sensor is measured over time, and correlated to the substance to be detected.

The theoretical basis for change in index of refraction in a material can be described by using the Lorentz-Lorentz formula. When the index of refraction (n) is defined with the Lorentz-Lorentz formula, the relationship between the polarizability (a) of the material and the number of molecules per unit volume (N) can be shown in equation (1).

$$\frac{n^2-1}{n^2+2} = \frac{4}{3}\pi na \qquad (1)$$

It is apparent that if the density and or the polarization of the material changes, the index of refraction of the material will change. For example, for a material that swells by absorbing liquids or gases, the number of molecules per unit volume will decrease, and thus the index of refraction will also decrease.

Changes in spatial atomic construction characteristics, substituent or solvent effects, and other physical or chemical effects of the material can have an effect on its polarization. Consequently, the two effects, e.g., the changes in material density and or polarization can be used for detection of chemicals.

At normal conditions where the chemicals to be detected do not exist, the clad in the optical fiber maintains a large index of refraction and functions in a light leakage mode. In the light leakage mode, the transmitted light leaks between the clad and the core within the sensor and total reflection does not occur.

When a substance to be detected exists, the index of refraction in the optical fiber is reduced due to the effect from the material, and the fiber functions in a wave guide mode. In this mode, total reflection occurs between the core and the clad like that of an ideal optical fiber. After the sensor theory was developed, the present invention focused on finding materials whose index of refraction can change to allow the sensor to go from the light leakage mode to wave guide mode so that the chemical or physical types of substances can be detected with high sensitivity.

One method to change the index of refraction in material is the use of polymers that swell when in contact with certain substances. Swelling decreases the number of molecules per volume, and decreases the index of refraction. There are many applications for the sensor described in the present invention. For example, the sensor may be used to detect various types of naturally occuring or synthetic organic compounds such as gasoline, kerosene, jet fuel, hydrocarbons, alcohol, ketones, amines, nitro-compounds, halogens, ethers, esters, inorganic materials such as silicones, etc., as well as water solutions containing the previously stated organic or inorganic compounds, and other various types of chemical or biological materials. Since the sensor is not electrically driven and is simple to form into devices, application to many fields is also possible. Examples include detecting gas tank leakage, detecting organic compounds in rivers or sewage, detecting propane gases in homes, precision air monitoring in clean rooms, temperature control or monitoring of greenhouses or animal housing, humidity monitoring during the food dehydration process, water leakage monitoring in semiconductor plants or electric and optical transmission cables, monitoring pollution, detecting poison gases such as arsine and silicone, detecting various gas-like high pressure gas, monitoring liquid storage tanks and concentration monitoring during chemical vapor deposition. Furthermore, as examples will show, very high sensitivity is possible for the sensor in the present invention.

DETAILED DESCRIPTION OF THE INVENTION

Figure 4:
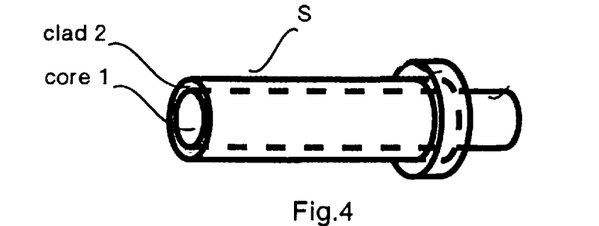
FIG. 4 is an illustration of the sensor S of the present invention.
Figure 5:
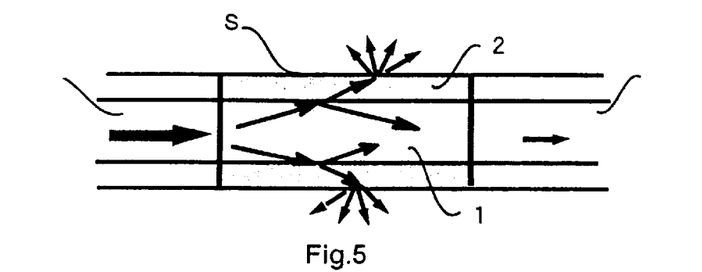
FIG. 5 is a schematic of the sensor S in light leakage mode. The arrows in the figure show the light being lost through the outer surface of the clad material.

In a preferred embodiment, FIG. 4 shows the fiber optic sensor of the present invention which comprises a fiber optic core having an index of refraction $n_{co}$ and a fiber optic clad surrounding and adjacent to the core, the clad having an index of refraction $n_{cl}$ which is greater than or equal to $n_{co}$. FIG. 5 illustrates an attempt to transmit light of a uniform wavelength from a first end of the sensor to an opposite, second end. During transmission, however, some of the light passes through or leaks ("light leakage mode") from the outer surface of the fiber optic clad. As a result, the intensity of the light reaching the second end of the sensor will be much less than the original intensity of the light entering the first end.

Figure 6:
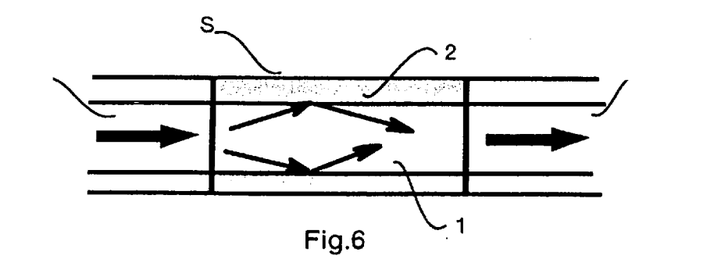
FIG. 6 is a schematic of the sensor S in wave guide mode. The arrows in the figure show the light being transmitted under total reflection through the core material.

However, if the fiber optic sensor is exposed to a specific environment, either biological or chemical, the fiber optic clad may swell, causing its volume to increase, and/or the clad's polarization may be reduced. The increased volume and/or reduced polarization will cause the clad's index of refraction $n_{cl}$ to decrease. Further, if the clad's index of refraction $c_{cl}$ decreases to a value less than the fiber optic core's index of refraction $n_{co}$, the sensor, as shown in FIG. 6, will then exhibit a vastly improved light transmission capability, in that most of the light entering the sensor's first end will exit from the second end (wave guide mode). By measuring the changes in total optical light output or intensity, both quantitative and qualitative analysis of the substance being detected is possible. The reaction between the substance to be detected and the clad can then occur rapidly. This rapid reaction with corresponding structure and polarizability changes in the clad material results in rapid change form $n_{co} \leq n_{cl}$ to $n_{co} > n_{cl}$, and the rapid change from light leakage mode to the wave guide mode, providing a definitive analysis and a visually apparent manner of detecting the substance. The changes in light intensity may further be measured as a function of the response time which equals the time it takes the sensor to change from light leakage mode to wave guide mode.

Thus, according to the present invention, the sensor's core and clad materials should be selected such that the clad's index of refraction will decrease to a value less than or equal to the index of refraction of the core, when the sensor is exposed to the material to be detected. The rate that the clad swells or reacts depends upon the reaction between the clad and the substance to be detected as well as the degree of polymerization of the clad material. If the molecular weight of the clad material is low, then the time required for the measurement is short. However, a very low molecular weight clad will act similar to a sponge when exposed to the substance and will not swell, and may gel or melt. The desirable clad material is a polymer with low molecular weight which is doped or blended so that the low molecular weight polymer will exist only inside the clad or at the surface. If the low molecular weight polymer exists at the surface, it is desirable for some to exist inside the clad also. The following are examples of materials that can be used in the present invention when requirements such as those stated are considered.

Experimentation has demonstrated that it is preferable that the fiber optic sensor's clad should be made from polymers which have exceptionally reactive groups such as free radicals or organics. It is especially desirable to use polymers with reactive groups as the main or the side chain of the polymer. Specifically, clad materials which are able to detect hydrocarbons are: catalyzed natural rubber, polypropylene, polyisobutane, polyisoprene, polybutadiene, polyethylvinylether, polystyrene, polymethylstyrene, polyethylene, and novolak. Detection of water and alcohol is possible using a clad material made from polymers which possess —OH, —COOH, —NHR (where R is an alkyl base or an aryl base), polyvinylalcohol, 12% sapnated polyvinylalcohol, polyacryloxide polymetacryloxide, polyethyleneoxide, urea formaldehyde resin and polyacrylamide. And, a clad material which can be used to form a sensor to detect ketones in the present invention include the following polymers: polybutadiene, polydiallylphthalate, polyvinyloxide, polyvinylchloride, polyethylvinylether, polymethylvinylketone, polymetacrylmethyloxide, polysurfone, polyethylene, polyacetyl, and polyacetyl.

After the clad materials are selected, then core materials are chosen with an index of refraction which meets the requirement of the present invention. For example, the index of refraction of polyisoprene in its non-swollen state is 1.52. When it swells from exposure to the hydrocarbon gas, then the index of refraction will go down to 1.46. Thus, to use polyisoprene as the clad material to detect the hydrocarbon gas, the core material must have an index of refraction between 1.46 and 1.52. As the difference in the index of refraction becomes narrower, the switch from $n_{co} \leq n_{cl}$ to $n_{co} > n_{cl}$ becomes faster.

In addition to the index of refraction requirements, the core material in the present invention should be chosen so that it will have excellent structural strength, and chemical and physical stability. Some of the polymers that meet this requirement for the core material are glass, norbornadiene type polymers, carbonate type resins, and methacrylate or acrylate type resins. In addition, polymers described above for use in the clads can also be used for the core, depending on the requirement of the particular sensor of the present invention.

The fiber optic sensor described in the present invention can easily be made into devices, and manufactured at low cost. The fiber optic sensor core can be fabricated from a plastic fiber optic, which can be immersed into a solution of the clad material and dried. Also, the clad may be formed by spin coating the clad and the core.

Figure 9:
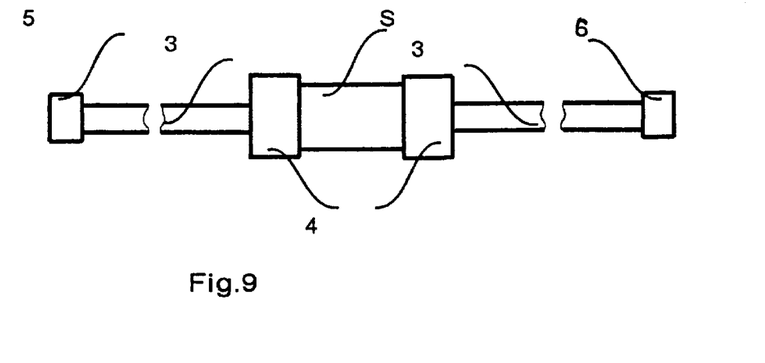
FIG. 9 shows the optical fiber sensor S connected to a fiber optic light source and a light detector.

FIG. 9 illustrates a typical arrangement of the fiber optic sensor as part of a light source means and a light intensity detection means. A pair of conventional fiber optic materials, 3 and 3a, are connected to each end of the fiber optic sensor S by means of a pair of connectors, 4 and 4a, a light emitter 5, such as an LED, is attached to an unconnected end of one of the conventional fibers and a light detector 6, such as a photodetector, is attached to the unconnected end of the other conventional fiber. Not shown in FIG. 9 is an alternate embodiment in which the light detector 6 and its associated conventional fiber are replaced with a light detector located adjacent to the sensor's outside surface and between its two ends. This detector measures the decrease in light intensity in order to detect the presence of the substance. In a preferred embodiment, the fiber optic sensor is between 20 and 30 mm in length.

Figure 7:
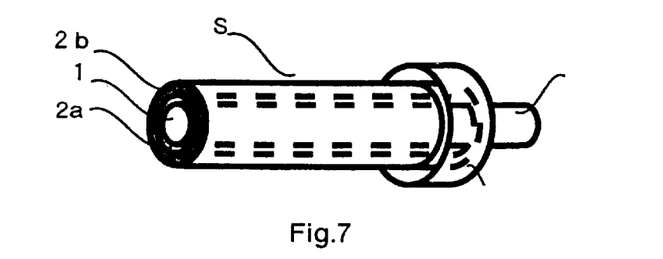
FIG. 7 is a schematic of the sensor S in the present invention with a multilayer clad construction.

As shown in FIG. 7, the fiber optic sensor of the present invention may also contain at least one additional fiber optic clad which surrounds and is adjacent to the clad which surrounds and is adjacent to the core. In this two-layer configuration, a first clad layer adjacent to the core is made of a material which has an index of refraction greater than that of the core, and after exposing the clad to the substance to be detected, the clad's index of refraction decreases to a value less than the core's refraction index. A second, outer clad layer is made of a material which will swell when exposed to the substance to be detected. When the second layer swells, a gap or space forms between the first and second clads, and the substance to be detected flows into this gap or space. The first clad layer is now exposed to the substance, which, in turn, causes the index of refraction of the first clad layer to decrease to a value less than the core's refractive index. In this two-layer clad design, the second clad layer acts as a screening device in that it is chosen such that it will only allow the substance to be detected to come into contact with the first clad. This feature of the present invention is particularly useful when the substance to be detected is in an environment containing other substances which, if allowed to come into contact with the first clad, would react with the first clad and potentially contaminate the results.

Figure 8:
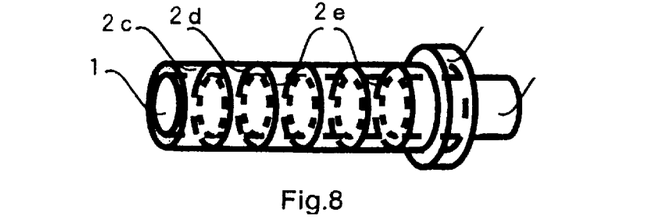
FIG. 8 is a schematic of the sensor S in the present invention with a clad that is made from several materials, arranged axially in an array.

In addition to detecting the existence of a substance in an environment, the fiber optic sensor of the present invention may also be used to detect more than one substance and the concentration of substances. As illustrated in FIG. 8, a plurality of fiber optic clads surrounding a fiber optic core are arranged axially in an array along the core. The material of each clad is selected such that each clad's swelling and reactivity characteristics will be different from the other clads, depending upon the chemical being detected. When the sensor containing the array of clads is exposed to a substance to be detected, the index of refraction of some, but not all, of the clads will decrease to a value less than or equal to the core's index of refraction. When light is transmitted through the sensor's core, some of the light will pass through in wave guide mode, depending upon how many clads have acquired an index of refraction less than or equal to the core's refractive index. Light detectors, located adjacent to the outside surface of each clad, measure the change in light intensity leaking through the clad. When a specific clad changes from light leakage mode to wave guide mode, the light intensity being measured by the detector will significantly decrease. The detector is calibrated to take into account the potential loss of light from exposure to prior clads. This feature of the invention provides for the detection of more than one chemical or biological substance using the same sensor.

Figure 10:
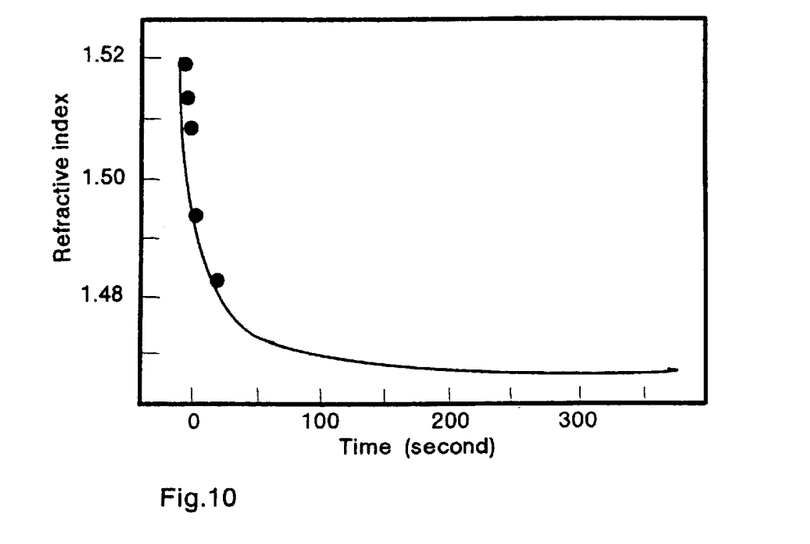
FIG. 10 shows the change in index of refraction after polyisoprene is immersed in acetone. Initially, the index of refraction decreases approximately linearly. After about 50 seconds, index of refraction decreases by about 0.04.
Figure 11:
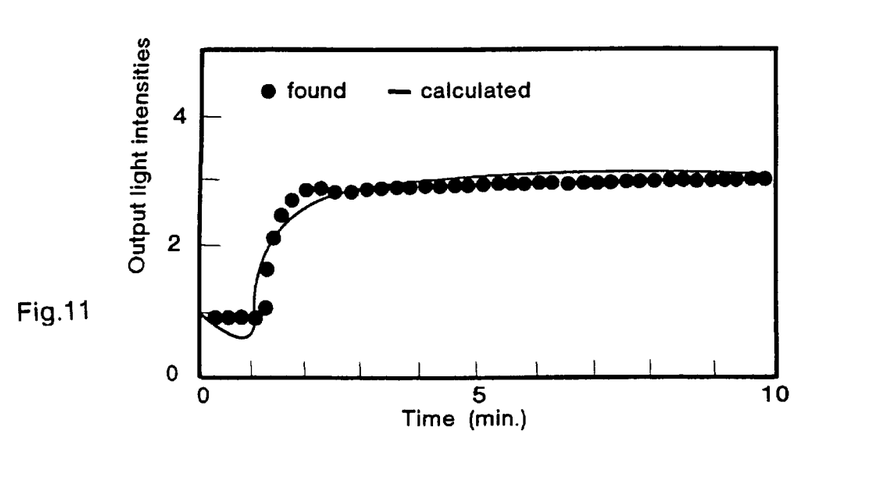
FIG. 11 is a graph showing the theoretical time and actual measurement time versus light output response for 50% acetone in water solution. After 1 min, there is a change in emitted light intensity. After 2 minutes, a constant value of light intensity was reached. The theoretical and actual values match, and the detection was done very quickly.

FIG. 10 is a graph showing the changes in the index of refraction of the isoprorene dipped in 100% acetone. This graph shows that initially, the index of refraction of the isoproprene decreases in a straight line. After about 50 seconds, the index of refraction of isoproprene decreased by about 0.04. FIG. 11 shows the both the calculated and the actual response time required to detect the acetone composition in the 50% acetone solution. After 1 min. of the exposure of the sensor to the solution, there is already a change in the output light intensity of the device. After 2 min, the output light intensity reached a steady value and the calculated and the actually measured values were identical. This example show that the measurements using the sensor in the present invention can be done very rapidly.

Figure 12:
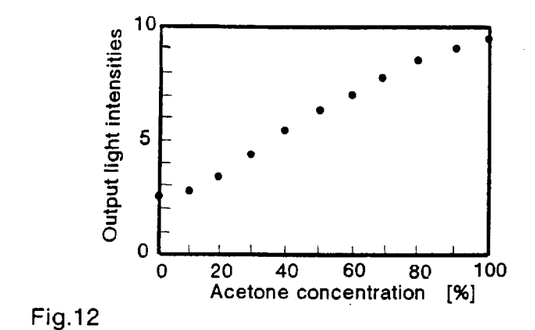
FIG. 12 shows the relationship between the output light intensity and the acetone concentration in the solution. The graph shows that the output light intensity increases proportionately with the acetone concentration.
Figure 13:
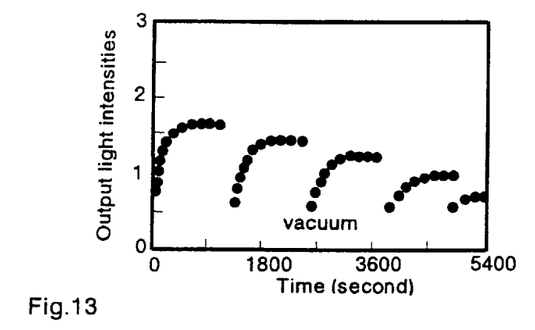
FIG. 13 is a plot of experimental output light intensity versus response time in seconds when measuring heptane concentration in a vacuum.
Figure 14:
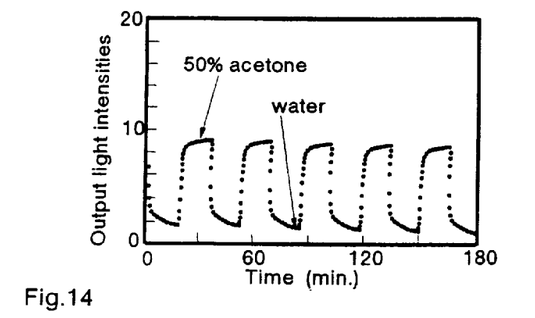
FIG. 14 is a plot of the output light intensity versus response time in minutes when the sensor is exposed to 50% acetone, removed after a few minutes, and exposed again. These procedures were repeated for a total time of 180 minutes.
Figure 15:
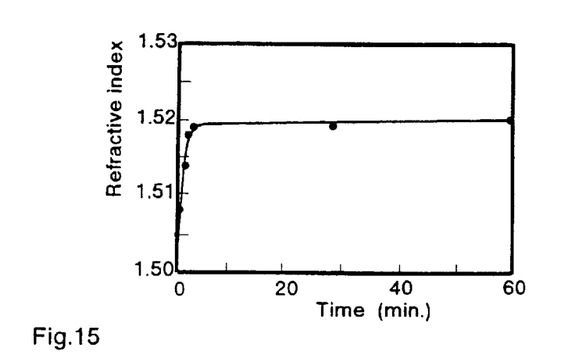
FIG. 15 is a plot of refractive index versus response time in minutes when the sensor is exposed to air.

FIG. 12 shows that change in the output light intensity with change in the acetone concentration in the solution. This graph shows that the output intensity increases proportionately with the acetone concentration.

The sensor in the present invention can detect several different types of chemical species even if only one type of clad is used around the core. This is possible if the clad has different response times for each of the various chemical species to be measured.

The sensor in the present invention can return to the light leakage mode when the detection process of the substance to be detected is completed. For example, after the acetone is detected using the above methods, the sensor will return to the light leakage mode upon exposure to air. In cases when non-reversible reaction between the substance to be detected occurs with the clad, an exposure of the sensor to the ultraviolet (UV) or visible light can force a dissociation reaction between the substance and the clad material. Sensor for halogen or poisonous gases are exposed to the UV or visible light in this way so that the sensors can be used over again.

Theoretical Description of the Invention

The detailed mechanism of the optical sensor described in the present invention is now described.

As polyisoprene swells, the change in its index of refraction as well as the optical light output was determined to see whether the polyisoprene can be used as the clad of the sensor in the present invention.

When material A permeates material B, then the index of refraction (n) of material A will change as the following equation:

$$n = \frac{n_o n_\infty}{(n_o - n_\infty)N + n_\infty} \quad (2)$$

Where n is the index of refraction when B penetrates A, N is the concentration of B in A $n_o$ is the index of refraction of A when B has not penetrated A (at time t=0)

$n_{co}$ is the index of refraction of A when B has completely penetrated A at infinite time (t=x)

If we assume that the concentration of B at time t and distance x from the surface of A is N (x, t), then the diffusion equation is shown in (3):

$$\frac{\partial v(x,t)}{\partial t} = D \frac{\partial^2 N(x,t)}{\partial x^2} \quad (3)$$

Figure 1:
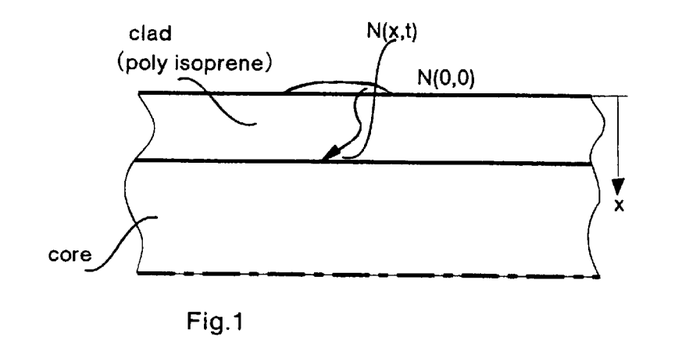
FIG. 1 is a schematic of the fiber optic sensor showing the clad material surrounding the core.

The schematic of the clad layer isoproprene on the core is shown in FIG. 1. where the initial condition; N(x, 0)=0

N(x, t)=No and D=diffusion constant of B in A

The solution to equation (3) is shown in (4). The equation defines the index of refraction of the clad and time t and distance x. Distance x is measured from the outer surface of the clad.

$$N(x, t) = N_o \left(1 - \frac{2}{\sqrt{\pi}} \int \frac{x - w^2}{2\sqrt{Dt}\, l} dw\right) \quad (4)$$

When (4) is placed in (2) then equation (5) below results.

$$N(x, t) = \frac{n_o n_\infty}{(n_o - n_\infty)N_o\left(1 - \frac{2}{\sqrt{\pi}} \int \frac{x - w^2}{2\sqrt{Dt}\, l} dw\right) + n_\infty} \quad (5)$$

The parameters $n_o$, $n_x$, No and D are all material properties that are constants. Thus, the relationship between the index of refraction $n_c$ at time t as material A permeates material B can be determined using the equation (5).

Next, we determine the optical output intensity using ray tracing method. The reflectivity coefficient between at the border between the core and the clad is used in the calculation. The reflectivity depend on n (the index of refraction of the A) and the angle of reflection).

$$P = R * Pi \quad (6)$$

where Pr is the intensity of the reflected wave, and is a function of f∂ and n;

Pi is the intensity of the incoming wave

R is the degree of reflection and is a function of n(x, t)

The total intensity of the optical output the sum of all reflected waves and is shown in equation (7) using f∂ and No as a parameter;

$$P_{total} = xP(t)\ P1(t) + P2(t) + P3(t) + \quad (7)$$

Figure 2:
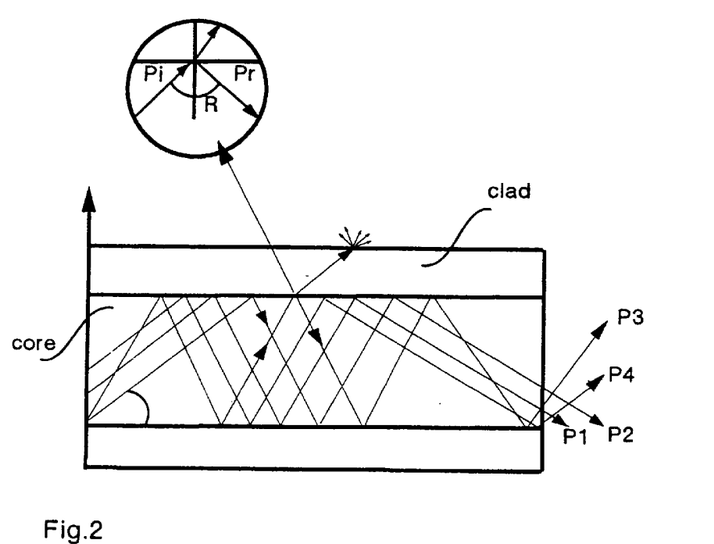
FIG. 2. is a schematic showing various reflected waves in the core and the clad. Pr is the intensity of the reflected wave, Pi is the intensity of the incoming wave, and R is the degree of reflection.

FIG. 2 is a schematic showing various reflected waves in the core and the clad.

The interpretation of the equation is as follows: as time t progresses, $n_{cl}$ becomes smaller, and R becomes larger. Thus, $P_{total}$, the total optical output intensity becomes larger, and the sensor transforms from the light leakage mode to the wave guide mode.

Figure 3:
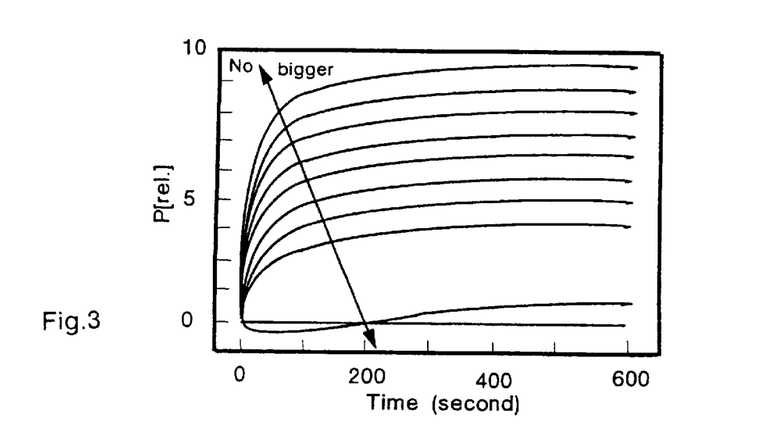
FIG. 3 is a plot of a simulation of the relative optical intensity as a function of time when acetone is the substance being detected. The sensor used isoprene as the clad material.

As an example, FIG. 3 shows a simulation result using acetone as the material to be detected and polyisoprene as the clad material. The theoretical value indicates that the response characteristic of the polyisoprene to swelling is excellent. This result also indicates that the present invention is supported from the theory. The detection of the targeted material is possible from changes in the optical characteristics by changing from the light leakage mode (no reflection) to the wave guide mode (total reflection).

EXAMPLES

Example 1

Method to Measure Hexane

Plastic fiber core made of Atone (made by Fujitsukasei) with an index of refraction of 1.51 was used as the core material. Polyisoprene with molecular weight of 410,000 and index of refraction of 1.52 was used as the clad material.

A film of thicknesses of 4 μm, 6 μm and 8 μm was spin coated from the isoprene solution. These films were attached to the Atone core with diameter of 1 mm and length of 20 mm. FIG. 4 shows the core 1 and clad 2 and the resulting sensor S.

Figure 16:
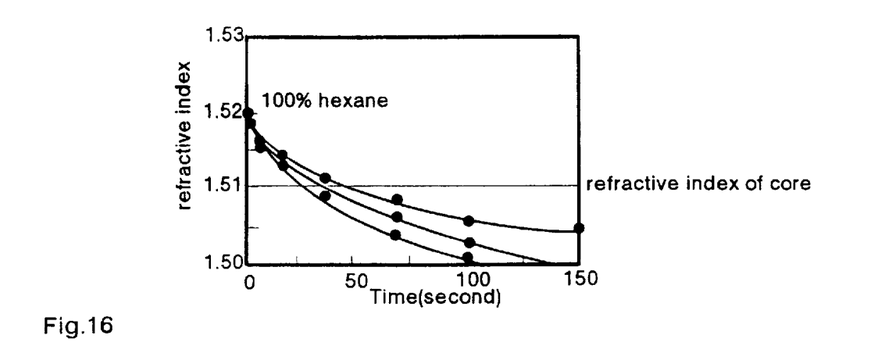
FIG. 16 is a plot of the refractive index versus response time in minutes when the sensor's clad with different thicknesses is exposed to 100% hexane. The refractive index of the core is 1.51.
Figure 17:
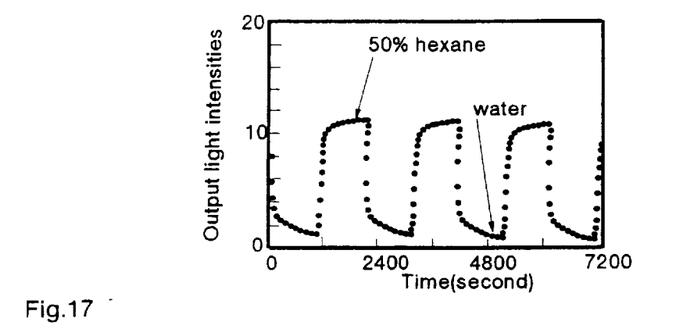
FIG. 17 is a plot of the output light intensity versus response time in minutes when the sensor is exposed to 50% hexane, removed after a few minutes, and exposed again. These procedures were repeated for a total time of 180 minutes.
Figure 18:
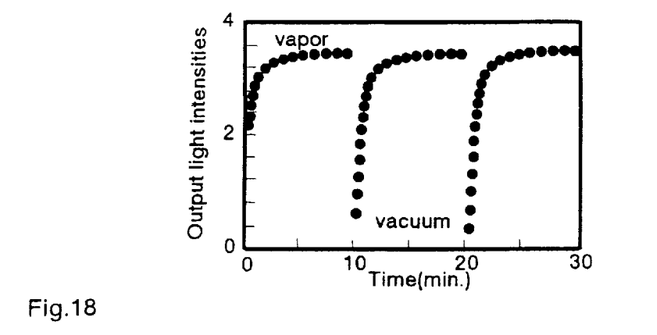
FIG. 18 is a plot of the output light intensity versus response time in minutes when the sensor is exposed to hexane vapor, removed after a few minutes, and exposed again. These procedures were repeated for a total time of 180 minutes.

The sensor S was made into sensor device shown in FIG. 9. Hexane was measured using this system, and the result is shown in FIGS. 16 to 18.

When the sensor S is exposed to hexane, the index of refraction of clad 2 will begin to decrease. The index of refraction changes of $n_{co} \leq n_{cl}$ to $n_{co} < n_{cl}$ occurs. The sensor changes from the light leakage mode to the wave guide mode. The light output intensity will increase considerably as measured by light detector such as a photodetector (6) in FIG. 9. The large light output shows that the hexane detection using this sensor and method is possible.

The response time changes with the thickness of the clad. If the changes in light emission are measured by placing a light detector such as a photodetector around the clad2 surface which is then exposed to a substance, the output intensity will decrease to zero. This is because the index of refraction of clad 2 will decrease, $n_{co} \leq n_{cl}$ will change to $n_{co} < n_{cl}$, and the sensor will change from the light leakage mode to the wave guide mode, and the light emission from the surface of the clad will be zero. Hexane can be detected using this method also.

Example 2

Method to Measure H₂O

Figure 19:
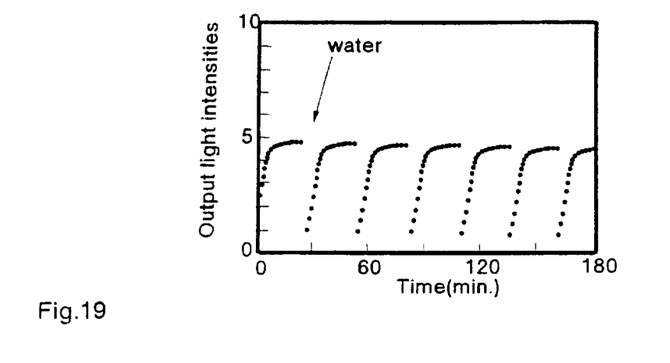
FIG. 19 is a plot of the output light intensity versus response time in minutes when the sensor is exposed to water, removed after a few minutes, and exposed again. These procedures were repeated for a total time of 180 minutes.

A solution of 10% polyvinyl alcohol (PVA) in water is coated on the surface of the plastic fiber core Atone (made by Fujitsukasei). Atone with an index of refraction of 1.51 is used as the corel material. After the water evaporates, PVA is cross linked by immersing the coated core into a solution of 1 M hydrochloric acid with 5% aqueous glutaraldehyde for 10 min. at 30° C. The coated PVA is 5 km, and becomes clad 2. The sensor S like one shown in FIG. 4 is formed. The sensor is used to form a sensor device as shown in FIG. 9. The result of using this system to measure $H_2O$ is shown in FIG. 19.

When the sensor is placed in the $H_2O$ environment, then the index of refraction of clad 2 decreases, and changes from $n_{co} \leq n_{cl}$ to $n_{co} > n_{cl}$. The sensor changes from light leakage mode to wave guide mode, and consequently, the light output intensity of light emitter like photodetector (6) increases making the detection of $H_2O$ possible.

Example 3

Method to Measure Diethylether

Novolak resin, the clad material, was fabricated as follows: 50 g of purified phenol, 37 ml of 37% formaldehyde aqueous solution, and 0.03 ml of aqueous solution of HCI (35%) for catalyst was added to a 500 ml four-necked flask. The flask is heated in an oil bath while the mixture is stirred. The mixture is refluxed for an additional 2 hours at 90° C. The reacted material is then transferred to an evaporation dish and precipitated in ice water.

Figure 20:
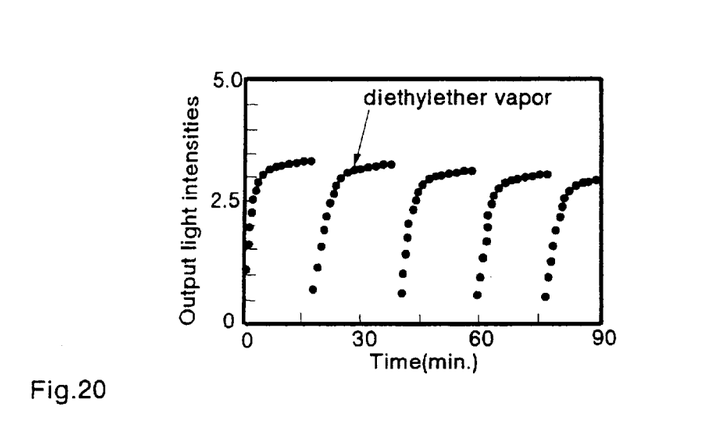
FIG. 20 is a plot of the output light intensity versus response time in minutes when the sensor is exposed to diethylether vapor, removed after a few minutes, and exposed again. These procedures were repeated for total time of 180 minutes.

This novolak polymer is coated around the corel material made from Atone to form a 5 μm clad 2 material. A sensor similar to that shown in FIG. 4 is formed. The sensor S was made into sensor device shown in FIG. 9. Diethylether was measured using this system, and the result is shown in FIG. 20.

When the sensor is placed in the diethylether environment, then the index of refraction of clad 2 decreases, and changes from $n_{co} \leq n_{cl}$ to $n_{co} < n_{cl}$. The sensor changes from light leakage mode to wave guide mode, and consequently, the light output intensity of light emitter like an A photodetector (6) in FIG. 9 increases making the detection of diethylether possible.

Example 4

Method to Measure HCl Gas 50 grams of distilled methacrylic oxide and 0.3 grams of reaction initiator AIBN is placed in the polymerization tube to fabricate polymethacrylate with phenolphtaline as the side chain. The sealed tube is frozen in liquid nitrogen to remove any atmosphere in the tube. The tube is then allowed to stand in an oil bath at 40° C. for 24 hours. The polymer that formed is taken out of the tube and purified by re-precipitation in water.

Under the nitrogen ambient, 50 ml of dehydrated tetrahydrofuran (THF) and 8.2 g of polymetacrylic acid is placed in a 500 ml four-necked flask cooled in ice water. Next, 12.2 g (96.1 mmol) of oxalyl chloride is slowly added to the mixture, and stirred for 24 hours at room temperature. Then a solution of 9.1 g (28.6 mmol) of phenylphthalene dissolved in THF is slowly added to the mixture and is stirred for 24 hours at room temperature. After the reaction is completed, the mixture is precipitated in cold water. The white polymer with cotton like texture is reprecipitated in water.

Figure 21:
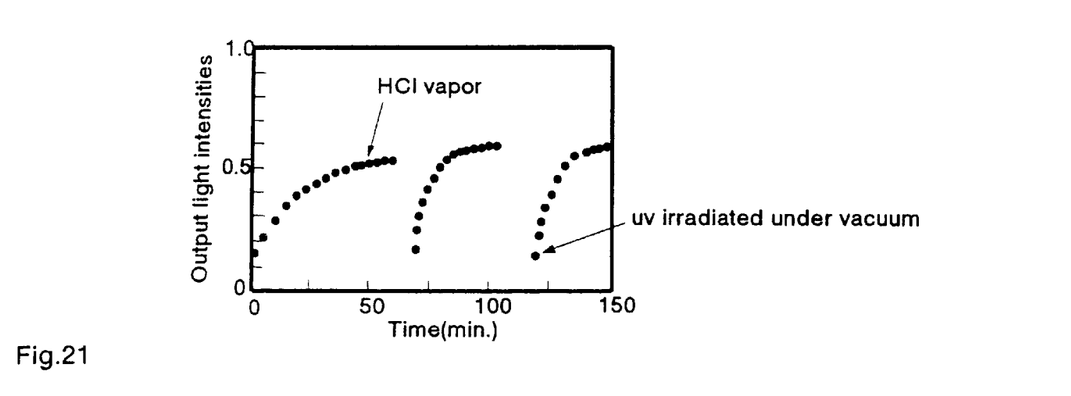
FIG. 21 is a plot of the output light intensity versus response time in minutes when the sensor is exposed to HCl vapor, removed after a few minutes and UV irradiated under vacuum, and exposed again. These procedures were repeated for a total time of 180 minutes.
Figure 22:
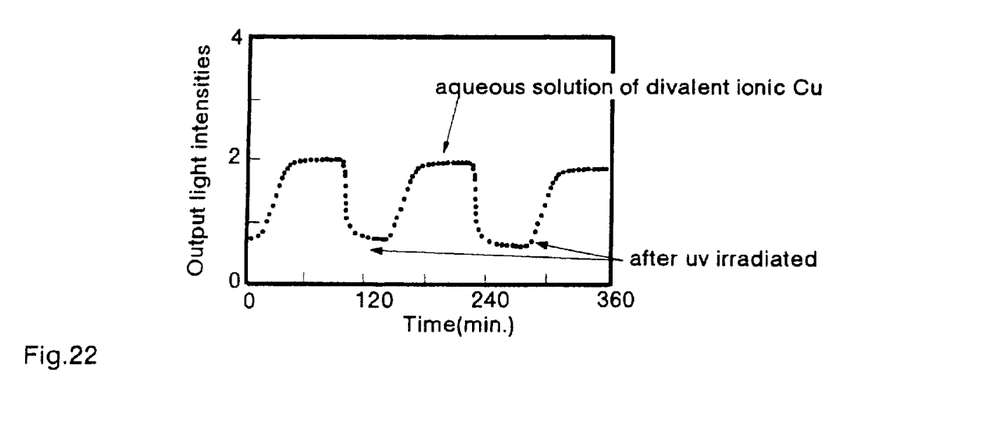
FIG. 22 is a plot of the output light intensity versus response time in minutes when the sensor is exposed to divalent ionic Cu, removed after a few minutes and UV irradiated, and exposed again. These procedures were repeated for a total time of 180 minutes.

This color polymer (index of refraction 1.54) is coated around Atone (index of refraction 1.51) core to form a 4 mm thick clad 2 layer. Sensor S for halogen type gases like one shown in FIG. 4 is formed. The sensor S was made into a sensor device like that shown in FIG. 9. Halogen gases were measured using this device, and the result is shown in FIG. 21.

The result shows that when the sensor S is placed in an HCl ambient, the index of refraction of clad 2 decreases, and changes from $n_{co} \leq n_{cl}$ to $n_{co} < n_{cl}$ occur. The sensor changes from light leakage mode to wave guide mode, and consequently, the light output intensity of light emitter like a photodetector (6) shown in FIG. 9 increases, making the detection of HCl possible.

We claim:

1. A fiber optic sensor comprising:
   (a) a fiber optic core having an index of refraction $n_{co}$, and
   (b) a fiber optic clad which is adjacent to and concentrically surrounding the core, said clad having an index of refraction $n_{cl}$, prior to exposing said clad to a substance to be detected, which is greater than or equal to the index of refraction $n_{co}$ of the core, whereby the index of refraction $n_{cl}$ of the clad decreases to a value less than the index of refraction $n_{co}$ of the core when the sensor is exposed to the substance to be detected.

2. The fiber optic sensor of claim 1 in which the clad is formed from a material which contains, as part of its chemical formula, a group which will react with the substance to be detected.

3. A fiber optic sensor comprising:
   (a) a fiber optic core having an index of refraction $n_{co}$, and
   (b) a plurality of fiber optic clads, each clad concentrically positioned relative to an adjacent clad with one of said clads concentrically positioned relative and adjacent to the core, said clad adjacent to the core having an index of refraction $n_{cl}$, prior to exposing said clad to a substance to be detected, which is greater than or equal to the index of refraction $n_{co}$ of the core, whereby the index of refraction $n_{cl}$ of said clad adjacent to the core decreases to a value less than the index of refraction $n_{co}$ of the core when the fiber optic sensor is exposed to the substance to be detected.

4. The fiber optic sensor of claim 3 in which the clad which is adjacent to the core is formed from a material which contains, as part of its chemical formula, a group which will react with the substance to be detected.

5. A fiber optic sensor comprising:
   (a) a fiber optic core having an index of refraction $n_{co}$, and
   (b) a plurality of axially aligned fiber optic clads which are adjacent to and concentrically surrounding the core, each clad having an index of refraction $n_{cl}$, prior to exposing each said clad to a substance to be detected, which is greater than or equal to the index of refraction $n_{co}$ of the core, whereby the index of refraction of one or more of said clads decreases to a value less than the index of refraction $n_{co}$ of the core when the fiber optic sensor is exposed to the substance to be detected.

6. The fiber optic sensor of claims 1, 2, 3, 4, or 5 further comprising:
   (a) the fiber optic sensor having a first end and second end;
   (b) a light source connected to first end of the fiber optic sensor; and
   (c) a light detector connected to the second end of the fiber optic sensor.

7. A method to detect a substance using an optical fiber sensor comprising steps of:
   (a) selecting a fiber optic core and fiber optic clad such that the index of refraction of the clad $n_{cl}$, prior to exposing said clad material to a substance to be detected, is greater than or equal to the index of refraction of the core $n_{co}$;
   (b) surrounding the fiber optic core with the fiber optic clad to form the optical fiber sensor having first and second ends;
   (c) illuminating light of a fixed intensity at the sensor's first end by means of a light source;
   (d) measuring the intensity of the light at the sensor's second end by means of a light detector;
   (e) exposing the sensor to the substance to be detected;
   (f) measuring the intensity of the light at the sensor's second end by means of the light detector; and
   (g) detecting an increase in light intensity at the sensor's second end.

8. The method of claim 7 in which the light detector means is a photodetector.

* * * * *